United States Patent [19]
Ferrand et al.

[11] Patent Number: 5,270,465
[45] Date of Patent: * Dec. 14, 1993

[54] 4(3H)-PTERIDINONE COMPOUNDS

[75] Inventors: Gerard Ferrand, Lyons; Herve Dumas, Villefontaine; Jean-Claude Depin; Yvette Quentin, both of Lyons, all of France

[73] Assignee: Lipha, Lyonnaise Industrille Pharmaceutique, Lyons, France

[*] Notice: The portion of the term of this patent subsequent to Dec. 1, 2009 has been disclaimed.

[21] Appl. No.: 970,839

[22] Filed: Nov. 3, 1992

Related U.S. Application Data

[62] Division of Ser. No. 501,104, Mar. 29, 1990, Pat. No. 5,167,949.

[30] Foreign Application Priority Data

Mar. 30, 1989 [FR] France .................. 89 04193

[51] Int. Cl.$^5$ .............................. A61K 31/505
[52] U.S. Cl. .................... 544/258; 544/407; 544/409; 544/257
[58] Field of Search ................ 514/249; 544/257, 258

[56] References Cited

U.S. PATENT DOCUMENTS

| | | | |
|---|---|---|---|
| 3,159,628 | 12/1964 | Pachter et al. | 544/257 X |
| 3,426,019 | 2/1969 | Pachter et al. | 544/257 X |
| 3,426,022 | 2/1969 | Nakanishi et al. | 544/257 |
| 3,732,224 | 5/1973 | Jacobs | 544/257 |
| 3,819,631 | 6/1974 | Broughton | 544/254 |
| 3,859,287 | 1/1975 | Parish et al. | 544/257 |
| 3,895,012 | 7/1975 | Liede et al. | 544/257 |
| 4,183,934 | 1/1980 | Paris et al. | 544/257 X |
| 4,361,700 | 11/1982 | Purcell et al. | 544/257 X |
| 4,701,455 | 10/1987 | Nichol | 514/249 |
| 5,167,949 | 12/1992 | Ferrand | 514/249 |

FOREIGN PATENT DOCUMENTS 2190447 2/1974 France .
1181284 2/1970 United Kingdom ............ 544/257

OTHER PUBLICATIONS

Ferrand et al. Chem. Abstr. vol. 114 entry 228957a (1990) Abstr. FR 2645152.
Journal of Medicinal Chemistry, vol. 15, 1972, pp. 210-211, American Chemical Society, Washington, D.C. U.S.; E. Felder et al: "Synthesis of 4(3H)-pteridinones".

Primary Examiner—Donald G. Daus
Attorney, Agent, or Firm—Browdy and Neimark

[57] ABSTRACT

The present invention relates to 4(3H)-pteridinones represented by the formula:

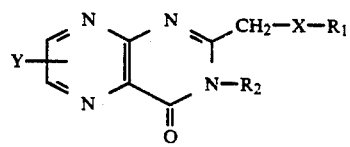

in which X is an oxygen atom or a sulphur atom, Y is a hydrogen atom, a lower alkyl radical, especially a methyl radical, at the 6-position or a hydroxyl group at the 7-position, $R_1$ is a hydrogen atom, a lower alkyl radical, a substituted or unsubstituted phenyl radical, a benzyl radical, a methoxymethyl group, an acetyl group, a 2-acetoxyethyl group or a 2,2,2-trifluoroethyl group and $R_2$ is a hydrogen atom or a lower alkyl radical, especially a methyl radical.

Application of these compounds as anti-allergic drugs.

7 Claims, No Drawings

4(3H)-PTERIDINONE COMPOUNDS

This is a division of copending parent application Ser. No. 07/501,104 filed Mar. 29, 1990 now U.S. Pat. No. 5,167,949.

The present invention relates to 4(3H)-pteridinones, to processes by means of which they may be prepared and to their application in the therapeutic field.

The biological role of 4(3H)-pteridinones is illustrated by the 2-alkyl-4(3H)-pteridinones described by V. Liede et al. in German Patent 2,232,098 and claimed for their diuretic and saluretic activity.

The compounds which are the subject of the invention are represented by the general formula I

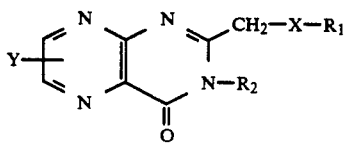

in which X is an oxygen atom or a sulphur atom, Y is a hydrogen atom, a lower alkyl radical, especially a methyl radical, at the 6-position or a hydroxyl group at the 7-position, $R_1$ is a hydrogen atom, a lower alkyl radical, a substituted or unsubstituted phenyl radical, a benzyl radical, a methoxymethyl group, an acetyl group, a 2-acetoxyethyl group or a 2,2,2-trifluoroethyl group and $R_2$ is a hydrogen atom or a lower alkyl radical, especially a methyl radical.

The term lower applied to an alkyl radical means that the radical may be linear or branched and that it can comprise from 1 to 4 carbon atoms.

The term substituted applied to a phenyl radical means that the radical may be substituted with one to three groups selected from lower alkyl, lower alkoxy, halogen, hydroxyl and acetyl.

The possible tautomeric forms of the compounds of the invention form an integral part of the invention. By way of example, but not exclusively, when Y is a hydroxyl group at the 7-position, the compounds of the invention of the formula Ia may also be written according to the tautomeric form of the formula Ib.

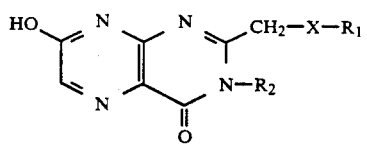

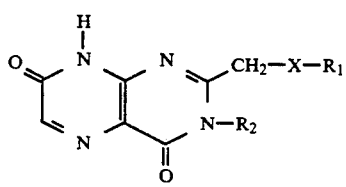

The compounds in the formula of which X is an oxygen atom, Y is a hydrogen atom or a hydroxyl group at the 7-position and $R_2$ is a hydrogen atom constitute a class of particular interest.

Preferred radicals $R_1$ are lower alkyl radicals, the phenyl radical or the benzyl radical.

The pharmaceutically acceptable salts also form an integral part of the invention. These can be alkali metal salts. These salts are obtained by treating the compounds of the invention with alkali metal hydroxides or carbonates. Alkali metals is understood to mean metals such as sodium or potassium.

The compounds of the invention may be prepared according to at least one of the following methods:

a) A 3-amino-2-pyrazinecarboxamide of the formula II

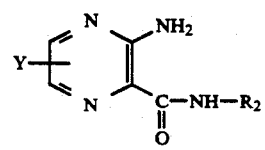

may be condensed with an ortho ester of the formula III

In the formulae II and III, X, Y, $R_1$ and $R_2$ have the meanings given above. In the formula III, $R_3$ is a lower alkyl radical, preferably an ethyl radical. The reaction is performed in acetic anhydride in the presence of an excess of ortho ester of the formula III. The temperature is the boiling point of the reaction mixture. The reaction time is generally between 1 and 3 hours.

b) When $R_2$ is a hydrogen atom, a 4-aminopteridine of the formula IV

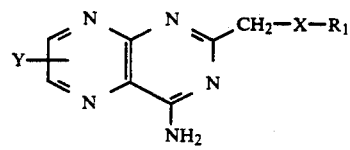

may be hydrolyzed in dilute aqueous alkali. In the formula IV, X, Y and $R_1$ have the meanings given above. The reaction is performed in water in the presence of a base such as sodium hydroxide or potassium hydroxide. The temperature can vary between room temperature and the boiling point of the reaction mixture, and preferably between 75° C. and the boiling point of the reaction mixture. The reaction time is generally between 10 minutes and 14 hours.

c) When Y and $R_2$ are hydrogen atoms, a 5,6-diamino-4(3H)-pyrimidinone of formula V

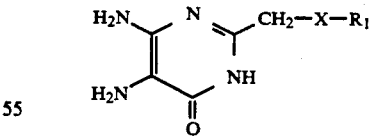

is condensed with glyoxal. In the formula V, X and $R_1$ have the meanings given above. The reaction is performed in water. The temperature can vary between room temperature and the boiling point of the reaction mixture. The reaction time is generally between 1 and 24 hours.

d) In the special case where X is an oxygen atom, Y is a hydrogen atom, $R_1$ a 2-acetoxyethyl group and $R_2$ a hydrogen atom, the corresponding compound of the invention I may be obtained by the hydrolysis followed by the acetylation of the compound IV for which X is an oxygen atom, Y a hydrogen atom and R₁ a 2-hydroxyethyl group.

e) In the special case where X is an oxygen atom and Y a hydroxyl group at the 7-position and where R₁ and R₂ are hydrogen atoms, the corresponding compound of the invention I may be obtained by hydrolysis of the compound of the same formula except for R₁, which represents an acetyl group.

The intermediate 3-amino-2-pyrazinecarboxamides of the formula II are known compounds. The intermediate ortho esters of the formula III are, in most instances, known compounds. Those which are new were prepared according to the usual techniques described, in particular, by S. M. McElvain and J. W. Nelson, J. Am. Chem. Soc. 1942, 64, 1825.

The intermediate 4-aminopteridines of the formula IV are new compounds. They are prepared by condensation of a 3-amino-2-pyrazinecarbonitrile of the formula VI

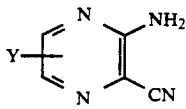

VI with an acetamidine of the formula VII

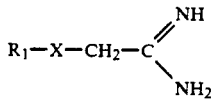

VII

In the formulae VI and VII, X, Y and R₁ have the meanings given above.

In the special case where X is an oxygen atom, Y a hydroxyl group at the 7-position and R₁ a methoxymethyl group, the corresponding 4-aminopteridine XI is obtained according to the reaction scheme below:

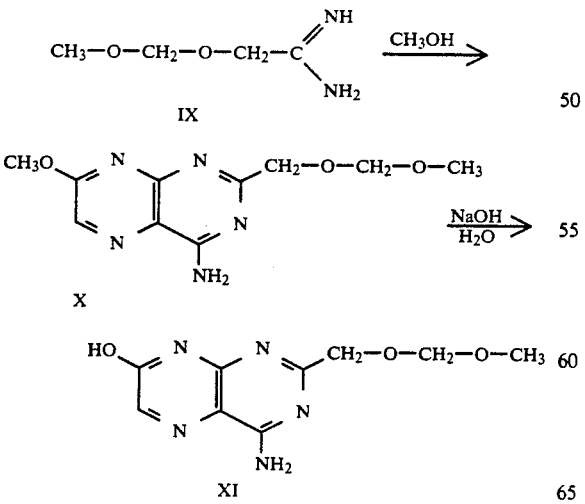

3-Amino-5-chloro-2-pyrazinecarbonitrile VIII is condensed with 2-(methoxymethoxy)acetamidine IX in the presence of methanol to give 4-amino-7-methoxy-2-(methoxymethoxymethyl)pteridine of the formula X. The methoxy group at the 7-position of the compound X may be hydrolyzed selectively in an alkaline medium to yield 4-amino-2-methoxymethoxymethyl-7-pteridinol of the formula XI.

The intermediate 3-amino-2-pyrazinecarbonitriles of the formula VI are known compounds. The intermediate acetamidines of the formula VII are, in some instances, known compounds. Those which are new were prepared according to the usual techniques, by reaction of ammonia with the alkyl acetimidates of the formula XII

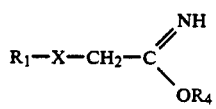

XII in an anhydrous low molecular weight alcohol such as methanol or ethanol In the formula XII, X and R₁ have the meanings given above and R₄ is an alkyl radical, preferably a methyl radical or an ethyl radical.

The intermediate alkyl acetimidates of the formula XII are, in some instances, known compounds. Those which are new were prepared according to the usual techniques described, in particular, by C. Djerassi and C. R. Scholz, J. Am. Chem. Soc. 1947, 69, 1688 and by F. C. Schaefer and G. A. Peters, J. Org. Chem,. 1961, 26, 412.

In the special case where X is an oxygen atom, R₁ a 2-hydroxyethyl group and R₄ an ethyl radical, the corresponding alkyl acetimidate XII is obtained according to a variant of the method of F. C. Schaefer and G. A. Peters, starting with (2-acetoxyethoxy)acetonitrile.

In the special case where X is an oxygen atom and where R₁ and R₄ are ethyl radicals, the corresponding alkyl acetimidate XII may be obtained by reaction of chloroacetonitrile with sodium ethoxide and ethanol.

The 5,6-diamino-4(3H)-pyrimidinones of the formula V are new compounds. They are prepared according to the reaction scheme below:

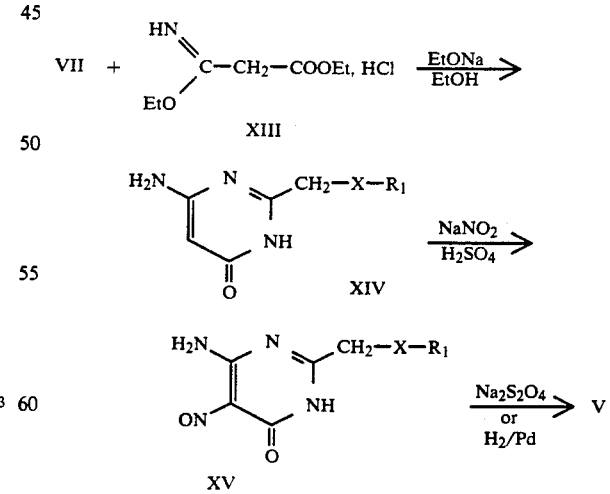

An acetamidine of the formula VII is condensed with the imino ether of ethyl cyanoacetate XIII to give a 6-amino-4(3H)-pyrimidinone of the formula XIV. These compounds XIV are nitrosated to 6-amino-5- nitroso-4(3H)-pyrimidinones of the formula XV Reduction of the compounds of the formula XV with sodium dithionite or by catalytic hydrogenation yields the 5,6-diamino-4(3H)-pyrimidinones V.

The compounds represented by the general formula I possess excellent anti-allergic properties, and are superior to known products, especially by virtue of being active when administered orally.

The anti-allergic activity was measured in rats by the passive cutaneous anaphylaxis or PCA test described by I. Mota, Life Sciences 1963, 7, 465 and Z. Ovary et al., Proceedings of Society of Experimental Biology and Medicine 1952, 81, 584.

In this test, the skin of rats is sensitized by 4 intradermal injections of a homologous anti-ovalbumin serum diluted 15-fold. On the day following sensitization, the animals receive 1 ml/kg of a 2.5% saline solution of Evans blue and 1 ml/kg of a 2.5% saline solution of ovalbumin simultaneously by intravenous injection. The test compounds are administered before the antigen, the time interval being 5 min by intraperitoneal injection and 10 min by the oral route. Thirty minutes after injection of the ovalbumin/dye mixture, the animals are sacrificed and the intensity of the allergic response is determined by measuring the area of skin coloration. The protection provided by the products of the invention is expressed as an $ED_{50}$ (dose decreasing by 50% the skin area occupied by the dye). Four rats are used for each dose of products.

The results obtained intraperitoneally for a few products of the invention are recorded in Table I.

TABLE I

| PRODUCT | PCA $ED_{50}$ (mg/kg/IP) |
|---|---|
| Example 1 | 7 |
| Example 3 | 14 |
| Example 4 | 9 |
| Example 7 | 21 |
| Example 9 | 39 |
| Example 11 | 10 |
| Example 12 | 18 |
| Example 13 | 14 |

The products showing the best results intraperitoneally were tested orally. These results are recorded in Table II.

TABLE II

| PRODUCT | PCA $ED_{50}$ (mg/kg/PO) |
|---|---|
| Example 1 | 24 |
| Example 3 | 33 |
| Example 4 | 25 |
| Example 11 | 48 |

The compounds described are distinguished, in addition, from known products by their long duration of action and by a capacity for anagonizing the effects of PAF-acether, especially its bronchoconstrictor effects. By way of illustration, the $ED_{50}$ of the compound described in Example 1 when administered intravenously is 0.068 mg/kg on the bronchospasm induced in anaesthetized guinea pigs by injection of 10 ng/kg/IV of PAF-acether.

The compounds of the invention exhibit low toxicity. By way of illustration, for the compound described in Example 1, the median lethal doses determined orally on rats and on mice are above 2,000 mg/kg, and the median lethal doses determined intraperitoneally and intraveneously on mice are above 1,600 mg/kg.

The present application also has as its subject the application of the compounds I by way of drugs, and in particular anti-allergic drugs. These drugs may be administered by inhalation in the form of aerosols, orally in the form of tablets, sugar-coated tablets or hard gelatin capsules, intravenously in the form of an injectable solution, cutaneously in the form of ointment, powder or solution or rectally in the form of suppositories. The daily dosages can vary from 1 to 50 mg of active principle taken by inhalation, from 5 to 250 mg of active principle taken orally, from 1 to 50 mg of active principle taken intravenously and from 20 to 400 mg of active principle taken rectally.

A few pharmaceutical formulations are given below by way of non-restrictive examples:

| Composition of a capsule for inhalation: | |
|---|---|
| active principle | 5 mg |
| Composition of an aerosol: | |
| active principle | 1 g |
| propellent gases | 99 g |
| Composition of a tablet: | |
| active principle | 50 mg |
| excipient: lactose, wheat starch, polyvidone, talc, magnesium stearate | |
| Composition of a hard gelatin capsule: | |
| active principle | 50 mg |
| excipient: lactose, wheat starch, talc, magnesium stearate | |
| Composition of an ampoule of injectable solution: | |
| active principle | 10 mg |
| excipient: sorbitol, water for injections qs | 5 ml |
| Composition of a suppository: | |
| active principle | 50 mg |
| semi-synthetic glycerides qs | 500 mg |
| Composition of an ointment: | |
| active principle | 0.5% |
| polyoxyethylene glycol glyceryl stearate | 15% |
| polyoxyethylenated saturated glycerides | 2% |
| liquid paraffin | 6% |
| water qs | 100% |

The examples which follow illustrate the invention without implied limitation. In the nuclear magnetic resonance (NMR) data, the following abbreviations were used: s for singlet, d for doublet; t for triplet, q for quartet and m for unresolved peaks; the chemical shifts $\delta$ are expressed in ppm.

Example 1

2-Ethoxymethyl-4(3H)-pteridinone

A mixture of 8.3 g (0.060 mole) of 3-amino-2-pyrazinecarboxamide [prepared according to R. C. Ellingson et al., J. Am. Chem. Soc. 1945, 67, 1711], 49.5 g (0.24 mole) of triethyl orthoethoxyacetate [prepared according to S. M. McElvain and P. M. Walters, J. Am. Chem. Soc. 1942, 64, 1963] and 53 ml of acetic anhydride is refluxed under a nitrogen atmosphere for 3 hours. The temperature of this reflux falls with the passage of time from 124° to 96° C. and then remains constant at the latter temperature. After cooling, the precipitate formed is isolated by filtration. It is washed with ether and recrystallized from ethanol. Yld: 5.5 g (44%), m.p. 168°–169° C.

| Percentage analysis: C₉H₁₀N₄O₂ (FW = 206.21) | | | |
|---|---|---|---|
| | C % | H % | N % |
| calculated | 52.42 | 4.89 | 27.17 |
| found | 52.14 | 4.91 | 27.34 |

IR: $\bar{\nu}(C=O) = 1690$ cm$^{-1}$

NMR (CDCl₃): δ = 1.3 (3H, t); 3.7 (2H, q); 4.6 (2H, s); 8.8 (1H, d); 8.9 (1H, d); 10.3 (1H, peak exchangeable with CF₃COOD).

EXAMPLE 2

2-Ethoxymethyl-4(3H)-pteridinone a) Methyl 2-ethoxyacetimidate

66.7 g (0.78 mole) of ethoxyacetonitrile [prepared according to L. Ramachandra Row and T. R. Thiruvengadam, Current Sci. 1947 (India), 16, 379] are added to a solution of sodium methoxide in methanol, obtained by reaction of 1.8 g (0.078 gram-atom) of sodium in 400 ml of methanol. The reaction mixture is stirred for 3 hours at room temperature. The sodium methoxide is then neutralized with a stream of carbon dioxide and the reaction mixture is thereafter concentrated under reduced pressure. The residue obtained is taken up with ether. The inorganic products are removed by filtration; the ethereal filtrate is concentrated and the residue is distilled under reduced pressure. Yld: 53.5 g (59%), b.p.₁₅38°-40° C.

NMR (CDCl₃): δ = 1.2 (3H, t); 3.5 (2H, q); 3.7 (3H, s); 3.8 (2H, s); 7.6 (1H, peak exchangeable with D₂O).

b) 2-Ethoxyacetamidine

53.5 g (0.457 mole) of methyl 2-ethoxyacetimidate are added to a solution, maintained at 10° C., of 39 g (2.29 moles) of ammonia in 1225 ml of absolute ethanol. The solution obtained is left for 6 days at room temperature and is then concentrated under reduced pressure. It is used in the next step without further purification. Yld: 46.7 g (quantitative).

c) 4-Amino-2-(ethoxymethyl)pteridine

A mixture of 36.0 g (0.30 mole) of 3-amino-2-pyrazinecarbonitrile [prepared according to A. Albert and K. Ohta, J. Chem. Soc. C, 1970, 1540] and 46.7 g of 2-ethoxyacetamidine in 700 ml of absolute ethanol is refluxed for 2 hours 30 minutes under a nitrogen atmosphere. After cooling, the precipitate obtained is isolated by filtration. It is purified by recrystallization from ethanol. Yld: 52.0 g (84%), m.p. 152°-154° C.

| Percentage analysis: C₉H₁₁N₅O (FW = 205.22) | | | |
|---|---|---|---|
| | C % | H % | N % |
| calculated | 52.67 | 5.40 | 34.13 |
| found | 52.56 | 5.37 | 34.04 |

NMR (DMSO-d₆): δ = 1.1 (3H, t); 3.5 (2H, q); 4.4 (2H, s); 8.2 (2H, peak exchangeable with CF₃COOD); 8.7 (1H, d); 9.0 (1H, d).

d) 2-Ethoxymethyl-4(3H)-pteridinone

A solution of 30.0 g (0.146 mole) of 4-amino-2-(ethoxymethyl)pteridine in 800 ml of 5% aqueous sodium hydroxide is brought slowly to 75° C. and maintained at this temperature for 2 hours. After cooling, the solution obtained is acidified with acetic acid to pH 6 and is then extracted with chloroform. The organic extracts are dried over sodium sulphate and concentrated to dryness under reduced pressure. The solid residue is recrystallized from ethanol in the presence of Norit. Yld: 19.5 g (65%), m.p. = 168°-169° C. The product is identical to that obtained in Example 1.

Example 3

2-Methoxymethyl-4(3H)-pteridinone

Obtained using the procedure described in Example 1, starting with 11.7 g (0.085 mole) of 3-amino-2-pyrazinecarboxamide, 73.0 g (0.38 mole) of triethyl orthomethoxyacetate [prepared according to E. T. Stiller, U.S. Pat. No. 2,422,598; C.A. 1947, 41, 5904a] and 75 ml of acetic anhydride. Yld: 12.3 g (75%), m.p. 187°-189° C. (ethanol).

| Percentage analysis: C₈H₈N₄O₂ (FW = 192.18) | | | |
|---|---|---|---|
| | C % | H % | N % |
| calculated | 50.00 | 4.20 | 29.15 |
| found | 49.92 | 4.10 | 29.12 |

IR: $\bar{\nu}(C=O) = 1690$ cm$^{-1}$

NMR (DMSO-d₆): δ = 3.4 (3H, s); 4.4 (2H, s); 8.8 (1H, d); 9.0 (1H, d); 12.7 (1H, peak exchangeable with CF₃COOD).

Example 4

2-Propoxymethyl-4(3H)-pteridinone a) Ethyl 2-propoxyacetimidate hydrochloride

Hydrogen chloride gas is bubbled for one hour into a solution, cooled to 0° C., of 29.7 g (0.30 mole) of propoxyacetonitrile [prepared according to D. Gauthier, Compt. Rend. Acad. Sci. 1906, 143, 831] and 13.8 g (0.30 mole) of absolute ethanol in 500 ml of ether. The reaction mixture is then left for 2 days at 0° C. and is thereafter taken up with 300 ml of ether. The precipitate formed is isolated by filtration. It is washed with ether and dried under reduced pressure; it is used in the next step without further purification. Yld: 30.2 g (55%).

b) Triethyl orthopropoxyacetate

30.2 g (0.17 mole) of ethyl 2-propoxyacetimidate hydrochloride are dissolved in 160 ml of absolute ethanol. The solution is left for 2 days at room temperature; it is then concentrated under reduced pressure. The residue obtained is taken up with ether and filtered. The ethereal solution is dried over potassium carbonate, filtered and concentrated under reduced pressure. The liquid obtained is used in the next step without further purification. Yld: 29.3 g (80%).

NMR (CDCl₃): δ = 0.9 (3H, t); 1.3 (9H, t); 1.3-2.0 (2H, m); 3.4 (2H, t); 3.5 (2H, s); 3.6 (6H, q).

c) 2-Propoxymethyl-4(3H)-pteridinone

Obtained using the procedure described in Example 1, starting with 4.6 g (0.033 mole) of 3-amino-2-pyrazinecarboxamide, 29.3 g (0.133 mole) of triethyl orthopropoxyacetate and 30 ml of acetic anhydride. Yld: 2.6 g (36%), m.p. 158°-160° C. (ethanol).

| Percentage analysis: C₁₀H₁₂N₄O₂ (FW = 220.23) | | | |
|---|---|---|---|
| | C % | H % | N % |
| calculated | 54.54 | 5.49 | 25.44 |

| Percentage analysis: $C_{10}H_{12}N_4O_2$ (FW = 220.23) | | | |
|---|---|---|---|
| | C % | H % | N % |
| found | 54.55 | 5.45 | 25.68 |

IR: $\bar{\nu}(C=O) = 1690$ cm$^{-1}$

NMR (DMSO-d$_6$): δ = 0.9 (3H, t); 1.3-2.0 (2H, m); 3.5 (2H, t); 4.4 (2H, s); 8.8 (1H, d); 9.0 (1H, d); 12.7 (1H, peak exchangeable with CF$_3$COOD).

Example 5

2-Methoxymethyl-3-methyl-4(3H)-pteridinone

A mixture of 7.8 g (0.0513 mole) of 3-amino-N-methyl-2-pyrazinecarboxamide [prepared according to W. F. Keir et al., J. Chem. Soc., Perkin Trans 1, 1978, 1002], 39.4 g (0.205 mole) of triethyl orthomethoxyacetate and 45.3 ml of acetic anhydride is refluxed under a nitrogen atmosphere for 3 hours. The temperature of this reflux falls with the passage of time from 114° to 90° C. and then remains constant at the latter temperature. After cooling, the reaction mixture is concentrated to dryness under reduced pressure. The residue obtained is purified by chromatography on a silica column (eluent: chloroform/methanol, 95:5 and then 90:10), and is then recrystallized from ethyl acetate. Yld: 5.0 g (47%), m.p. 130.5°-132.5° C.

| Percentage analysis: $C_9H_{10}N_4O_2$ (FW = 206.21) | | | |
|---|---|---|---|
| | C % | H % | N % |
| calculated | 52.42 | 4.89 | 27.17 |
| found | 52.51 | 4.94 | 27.17 |

IR: $\bar{\nu}(C=O) = 1690$ cm$^{-1}$

NMR (DMSO-d$_6$): δ = 3.4 (3H, s); 3.6 (3H, s); 4.7 (2H, s); 8.9 (1H, d); 9.0 (1H, d).

Example 6

2-Acetoxymethyl-4(3H)-pteridinone a) Ethyl 2-acetoxyacetimidate hydrochloride Hydrogen chloride gas is bubbled to saturation into a solution, cooled to 0° C., of 30.0 g (0.303 mole) of acetoxyacetonitrile [prepared according to L. Henry, Rec. Trav. Chim. Pays Bas 1905, 24, 169] and 15.4 g (0.334 mole) of absolute ethanol in 300 ml of ether. The reaction mixture is then left for 5 hours at 0° C. The precipitate formed is isolated by filtration. It is washed with ether and dried under reduced pressure; it is used in the next step without further purification. Yld: 52.2 g (95%), m.p. 100°-101° C.

NMR (DMSO-d$_6$+CF$_3$COOD): δ = 1.1 (3H, t); 1.7 (3H, s); 3.4 (2H, q); 3.8 (2H, s).

b) Triethyl orthoacetoxyacetate

A mixture of 34.0 g (0.187 mole) of ethyl 2-acetoxyacetimidate hydrochloride and 340 ml of absolute ethanol is left for 3 days at room temperature. The precipitate formed is removed by filtration; the filtrate is concentrated under reduced pressure. The residue obtained is taken up with 800 ml of ether and cooled to about −10° C. A new precipitate is formed, and is removed by filtration. The filtrate is concentrated under reduced pressure. The liquid obtained is used in the next step without further purification. Yld: 34.5 g 84%).

NMR (CDCl$_3$): δ = 1.0 (9H, t); 1.9 (3H, s); 3.4 (6H, q); 4.1 (2H, s).

c) 2-Acetoxymethyl-4(3H)-pteridinone

Obtained using the procedure described in Example 1, starting with 5.3 g (0.038 mole) of 3-amino-2-pyrazinecarboxamide, 34.5 g (0.157 mole) of triethyl orthoacetoxyacetate and 34.5 ml of acetic anhydride. Refluxing time: 1 hour 45 minutes. Yld: 5.4 g (65%), m.p. 210°-212° C. (ethanol).

| Percentage analysis: $C_9H_8N_4O_3$ (FW = 220.19) | | | |
|---|---|---|---|
| | C % | H % | N % |
| calculated | 49.09 | 3.66 | 25.45 |
| found | 49.02 | 3.73 | 25.56 |

IR: $\bar{\nu}(C=O) = 1670$ and $1720$ cm$^{-1}$

NMR (DMSO-d$_6$): δ = 2.2 (3H, s); 5.0 (2H, s); 8.8 (1H, d); 9.0 (1H, d); 13.8 (peak exchangeable with CF$_3$COOD).

Example 7

2-Ethoxymethyl-7-hydroxy-4(3H)-pteridinone

Obtained using the procedure described in Example 1, starting with 2.1 g (0.0136 mole) of 3-amino-5-hydroxy-2-pyrazinecarboxamide [prepared according to E. C. Taylor et al., J. Org. Chem. 1975, 40, 2341], 14.0 g (0.068 mole) of triethyl orthoethoxyacetate and 14.0 ml of acetic anhydride. Yld: 1.2 g (40%), m.p. 255°-256° C. (methanol/N,N-dimethylformamide).

| Percentage analysis: $C_9H_{10}N_4O_3$ (FW = 222.20) | | | |
|---|---|---|---|
| | C % | H % | N % |
| calculated | 48.65 | 4.54 | 25.21 |
| found | 48.88 | 4.56 | 25.14 |

IR: $\bar{\nu}(C=O) = 1640$ and $1690$ cm$^{-1}$

NMR (DMSO-d$_6$): δ = 1.1 (3H, t); 3.5 (2H, q); 4.3 (2H, s); 7.9 (1H, s); 12.7 (2H, broad peak).

Example 8

2-Acetoxymethyl-7-hydroxy-4(3H)-pteridinone

Obtained using the procedure described in Example 1, starting with 5.0 g (0.0324 mole) of 3-amino-5-hydroxy-2-pyrazinecarboxamide, 29.5 g (0.134 mole) of triethyl orthoacetoxyacetate and 9.5 ml of acetic anhydride. Refluxing time: 1 hour 45 minutes. Yld: 3.8 g (50%), m.p. >300° C. (ethanol/N,N-dimethylformamide).

| Percentage analysis: $C_9H_8N_4O_4$ (FW = 236.19) | | | |
|---|---|---|---|
| | C % | H % | N % |
| calculated | 45.77 | 3.41 | 23.72 |
| found | 45.79 | 3.65 | 23.84 |

IR: $\bar{\nu}(C=O) = 1625, 1690$ and $1735$ cm$^{-1}$

NMR (DMSO-d$_6$): δ = 2.2 (3H, s); 5.0 (2H, s); 7.9 (1H, s); 12.9 (2H, peak exchangeable with CF$_3$COOD).

Example 9

2-Phenoxymethyl-4(3H)-pteridinone a) 4-Amino-2-(phenoxymethyl)pteridine

Obtained using the procedure described in section c of Example 2, starting with 3.0 g (0.025 mole) of 3-amino-2-pyrazinecarbonitrile and 3.8 g (0.025 mole) of 2-phenoxyacetamidine [prepared according to C. Djerassi and C. R. Scholz, J. Am. Chem. Soc., 1947, 69, 1688] in 100 ml if absolute ethanol. Refluxing time: 4 hours. Yld: 5.4 g (85%), m.p. 202°–204° C. (ethanol).

| Percentage analysis: $C_{13}H_{11}N_5O$ (FW = 253.26) | | | |
|---|---|---|---|
| | C % | H % | N % |
| calculated | 61.65 | 4.38 | 27.65 |
| found | 61.28 | 4.22 | 27.37 |

NMR (DMSO-$d_6$): $\delta$=5.1 (2H, s); 6.6–7.6 (5H, m); 8.4 (2H, peak exchangeable with $CF_3COOD$); 8.8 (1H, d); 9.0 (1H, d).

b) 2-Phenoxymethyl-4(3H)-pteridinone

A mixture of 4.0 g (0.016 mole) of 4-amino-2-(phenoxymethyl)pteridine and 400 ml of 5% aqueous sodium hydroxide is brought slowly to 95° C. and maintained at this temperature for 2 hours. After cooling, the solution obtained is acidified with acetic acid to pH 5.5. The precipitate formed is isolated by filtration. It is purified by recrystallization from ethanol. Yld: 2.8 g (70%), m.p. 220°–221° C.

| Percentage analysis: $C_{13}H_{10}N_4O_2$ (FW = 254.25) | | | |
|---|---|---|---|
| | C % | H % | N % |
| calculated | 61.41 | 3.96 | 22.04 |
| found | 61.44 | 3.97 | 22.08 |

IR: $\overline{\nu}(C=O)=1690$ cm$^{-1}$
NMR (DMSO-$d_6$): $\delta$=5.0 (2H, s); 6.7–7.4 (5H, m); 8.7 (1H, d); 8.9 (1H, d); 12.8 (1H, peak exchangeable with $CF_3COOD$).

Example 10

2-[(2,3-Dichlorophenoxy)methyl]-4(3H)-pteridinone a) Ethyl 2-(2,3-dichlorophenoxy)acetimidate hydrochloride Obtained using the procedure described in section a of Example 6, starting with 219.8 g (1.086 moles) of (2,3-dichlorophenoxy)acetonitrile [prepared according to R. W. Fuller et al., J. Med. Chem. 1973, 16, 101] and 50.0 g (1.086 moles) of absolute ethanol in 1750 ml of ether. Reaction time: 16 hours at 0° C. Yld: 293.5 g (95%), m.p. 167°–169° C.

NMR (DMSO-$d_6$): $\delta$=1.3 (3H, t); 4.3 (2H, q); 5.1 (2H, s); 6.6 (1H, s exchangeable with $CF_3COOD$); 7.0–7.6 (3H, m); 8.3 (1H,s exchangeable with $CF_3COOD$).

b) 2-(2,3-Dichlorophenoxy)acetamidine hydrochloride 11.8 g (0.041 mole) of ethyl 2-(2,3-dichlorophenoxy)acetimidate hydrochloride are added rapidly to a solution, cooled to 10° C., of 3.5 g (0.21 mole) of ammonia in 100 ml of absolute ethanol. The reaction mixture is left for 3 days at room temperature. After removal of a few suspended particles by filtration, the reaction mixture is concentrated to dryness under reduced pressure. The solid residue obtained is purified by washing with ether and recrystallization from isopropanol. Yld: 8.0 g (75%), m.p. 204.5°–206.5° C.

| Percentage analysis: $C_8H_9Cl_3N_2O$ (FW = 255.53) | | | | |
|---|---|---|---|---|
| | C % | H % | Cl % | N % |
| calculated | 37.60 | 3.55 | 41.62 | 10.96 |
| found | 37.61 | 3.60 | 41.36 | 10.85 |

NMR (DMSO-$d_6$+$D_2O$): $\delta$=5.1 (2H, s); 7.1–7.7 (3H, m)

c) 2-(2,3-Dichlorophenoxy)acetamidine 8.0 g (0.031 mole) of 2-(2,3-dichlorophenoxy)acetamidine hydrochloride are suspended in sodium hydroxide solution and extracted with chloroform. The organic extract is concentrated to dryness under reduced pressure. The solid residue is washed with hexane and dried; it is used in the next step without further purification. Yld: 6.7 g (98%), m.p. 104°–108° C.

d) 4-Amino-2-[(2,3-dichlorophenoxy)methyl]pteridine

Obtained using the procedure described in section c of Example 2, starting with 3.6 g (0.030 mole) of 3-amino-2-pyrazinecarbonitrile and 6.6 g (0.030 mole) of 2-(2,3-dichlorophenoxy)acetamidine in 100 ml of absolute ethanol. Refluxing time: 14 hours. Yld: 8.1 g (84%), m.p. 216°–218° C. (ethanol).

| Percentage analysis: $C_{13}H_9Cl_2N_5O$ (FW = 322.15) | | | | |
|---|---|---|---|---|
| | C % | H % | Cl % | N % |
| calculated | 48.47 | 2.82 | 22.01 | 21.74 |
| found | 48.38 | 2.86 | 22.10 | 21.81 |

NMR (DMSO-$d_6$): $\delta$=5.2 (2H, s); 7.1 (3H, s); 8.3 (2H, peak exchangeable with $CF_3COOD$); 8.7 (1H, d); 9.0 (1H, d).

e) 2-[(2,3-Dichlorophenoxy)methyl]-4(3H)-pteridinone

Obtained using the procedure described in section b of Example 9, starting with 1.0 g (0.0031 mole) of 4-amino-2-[(2,3-dichlorophenoxy)methyl]pteridine in 35 ml of 5% aqueous sodium hydroxide. Heating time: 10 minutes under reflux. Yld: 0.5 g (50%), m.p. 219°–220.5° C. (ethanol).

| Percentage analysis: $C_{13}H_8Cl_2N_4O_2$ (FW = 323.14) | | | | |
|---|---|---|---|---|
| | C % | H % | Cl % | N % |
| calculated | 48.32 | 2.50 | 21.94 | 17.34 |
| found | 48.53 | 2.53 | 21.99 | 17.49 |

IR: $\overline{\nu}(C=O)=1680$ cm$^{-1}$
NMR (DMSO-$d_6$+$CF_3COOD$): $\delta$=5.1 (2H, s); 7.1 (3H, s); 8.7 (1H, d); 8.9 (1H, d).

Example 11

2-Benzyloxymethyl-4(3H)-pteridinone a) 4-Amino-2-(benzyloxymethyl)pteridine

Obtained using the procedure described in section c of Example 2, starting with 12.0 g )0.10 mole) of 3-amino-2-pyrazinecarbonitrile and 25.0 g (0.15 mole) of 2-(benzyloxy)acetamidine [prepared according to W. J. Haggerty Jr. and W. J. Rost, J. Pharm. Sci. 1969, 58, 50] in 400 ml of absolute ethanol. Refluxing time: 4 hours. Yld: 15.4 g (58%), m.p. 112°–114° C. An analytical sample was obtained by recrystallization from ethanol, followed by washing with dilute hydrochloric acid and finally recrystallization from ethyl acetate. M.p. 131°–133° C.

| Percentage analysis: $C_{14}H_{13}N_5O$ (FW = 267.29) | | | |
|---|---|---|---|
| | C % | H % | N % |
| calculated | 62.91 | 4.90 | 26.20 |
| found | 62.74 | 4.79 | 26.22 |

NMR (DMSO-$d_6$): $\delta$=4.6 (2H, s); 4.7 (2H, s); 7.1–7.6 (5H, m); 8.3 (2H, peak exchangeable with CF$_3$COOD); 8.8 (1H, d); 9.0 (1H, d).

b) 2-Benzyloxymethyl-4(3H)-pteridinone

Obtained using the procedure described in section b of Example 9, starting with 10.0 g (0.037 mole) of crude 4-amino-2-(benzyloxymethyl)pteridine in 300 ml of 5% aqueous sodium hydroxide. Heating time: 2 hours at 80° C. Yld: 8.2 g (83%), m.p. 157°–159° C. (ethanol).

| Percentage analysis: $C_{14}H_{12}N_4O_2$ (FW = 268.28) | | | |
|---|---|---|---|
| | C % | H % | N % |
| calculated | 62.68 | 4.51 | 20.88 |
| found | 62.85 | 4.39 | 21.15 |

IR: $\bar{\nu}$(C=O)=1680 cm$^{-1}$
NMR (DMSO-$d_6$): $\delta$=4.5 (2H, s); 4.6 (2H, s); 7.1–7.6 (5H, m); 8.8 (1H, d); 8.9 (1H, d); 12.7 (1H, peak exchangeable with CF$_3$COOD).

Example 12

2-Methoxymethoxymethyl-4(3H)-pteridinone a) Methyl 2-(methoxymethoxy)acetimidate

Obtained using the procedure described in section a of Example 2, starting with 286.8 g (2.84 moles) of methoxymethoxyacetonitrile [prepared according to D. J. Loder and W. M. Bruner, U.S. Pat. No. 2,398,757; C.A. 1946, 40, 3774] and 6.5 g (0.284 gram-atom) of sodium in 1430 ml of methanol. Reaction time: 2 days. Yld: 302.6 g (80%), b.p.$_{15}$62°–65° C.
NMR (CDCl$_3$): $\delta$=3.3 (3H, s); 3.7 (3H, s); 3.9 (2H, s); 4.6 (2H, s); 7.7 (1H, peak exchangeable with D$_2$O).

b) 2-(Methoxymethoxy)acetamidine

Obtained using the procedure described in section b of Example 2, starting with 20.0 g (0.15 mole) of methyl 2-(methoxymethoxy)acetimidate and 13.0 g (0.75 mole) of ammonia in 400 ml of absolute ethanol. Reaction time: 2 days. Yld: 18.0 g (quantitative).
NMR (CDCl$_3$+D$_2$O): $\delta$=3.4 (3H, s); 4.0 (2H, s); 4.6 (2H, s).

c) 4-Amino-2-(methoxymethoxymethyl)pteridine

Obtained using the procedure described in section c of Example 2, starting with 12.0 g (0.10 mole) of 3-amino-2-pyrazinecarbonitrile and 18.0 g (0.15 mole) of 2-(methoxymethoxy)acetamidine in 400 ml of absolute ethanol. Refluxing time: 4 hours. Yld: 15.8 g (71%), m.p. 129°–131° C. (ethanol).

| Percentage analysis: $C_9H_{11}N_5O_2$ (FW = 221.22) | | | |
|---|---|---|---|
| | C % | H % | N % |
| calculated | 48.86 | 5.01 | 31.66 |
| found | 49.02 | 5.20 | 31.61 |

NMR (DMSO-$d_6$): $\delta$=3.3 (3H, s); 4.5 (2H, s); 4.7 (2H, s); 8.2 (2H, peak exchangeable with CF$_3$COOD); 8.7 (1H, d); 8.9 (1H, d).

d) 2-Methoxymethoxymethyl-4(3H)-pteridinone

Obtained using the procedure described in section d of Example 2, starting with 5.3 g (0.024 mole) of 4-amino-2-(methoxymethoxymethyl)pteridine in 250 ml of 5% aqueous sodium hydroxide. Heating time: 2 hours at 80° C. Yld: 2.2 g (41%), m.p. 161°–163° C. (ethanol).

| Percentage analysis: $C_9H_{10}N_4O_3$ (FW = 222.20) | | | |
|---|---|---|---|
| | C % | H % | N % |
| calculated | 48.65 | 4.54 | 25.21 |
| found | 48.38 | 4.52 | 24.92 |

IR: $\bar{\nu}$(C=O)=1680 cm$^{-1}$
NMR (DMSO-$d_6$): $\delta$=3.2 (3H, s); 4.4 (2H, s); 4.7 (2H, s); 8.7 (1H, d); 8.9 (1H, d); 12.6 (1H, peak exchangeable with CF$_3$COOD).

Example 13

2-Isopropoxymethyl-4(3H)-pteridinone a) 2-Isopropoxyacetamidine

Obtained using the procedure described in section b of Example 2 starting with 14.7 g (0.112 mole) of methyl 2-isopropoxyacetimidate [prepared according to F. C. Schaefer and G. A Peters, J. Org. Chem. 1961, 26, 412] and 9.50 g (0.56 mole) of ammonia in 300 ml of absolute ethanol. Reaction time: 2 days. Yld: 13.0 g (quantitative).

b) 4-Amino-2-(isopropoxymethyl)pteridine

Obtained using the procedure described in section c of Example 2, starting with 8.8 g (0.073 mole) of 3-amino-2-pyrazinecarbonitrile and 13.0 g (0.11 mole) of 2-isopropoxyacetamidine in 295 ml of absolute ethanol. Refluxing time: 4 hours. Yld: 4.5 g (28%), m.p. 139°–141° C. (ethyl acetate).

| Percentage analysis: $C_{10}H_{13}N_5O$ (FW = 219.25) | | | |
|---|---|---|---|
| | C % | H % | N % |
| calculated | 54.78 | 5.98 | 31.94 |
| found | 54.88 | 6.17 | 31.83 |

NMR (CDCl$_3$): 1.3 (6H, d); 3.8 (1H, septet); 4.7 (2H, s); 8.2 (2H, peak exchangeable with CF$_3$COOD); 8.6 (1H, d); 9.0 (1H, d).

c) 2-Isopropoxymethyl-4(3H)-pteridinone

Obtained using the procedure described in section d of Example 2, starting with 4.5 g (0.0205 mole) of 4-amino-2-(isopropoxymethyl)pteridine in 150 ml of 5% aqueous sodium hydroxide. Heating time: 2 hours at 80° C. Yld: 3.0 g (66%), m.p. 198°–199° C. (ethanol).

| Percentage analysis: $C_{10}H_{12}N_4O_2$ (FW = 220.23) | | | |
|---|---|---|---|
| | C % | H % | N % |
| calculated | 54.54 | 5.49 | 25.44 |
| found | 54.24 | 5.20 | 25.29 |

IR: $\bar{\nu}$(C=O)=1690 cm$^{-1}$

NMR (CDCl$_3$): δ=1.3 (6H, d); 3.8 (1H, septet); 4.6 (2H, s); 8.7 (1H, d); 8.9 (1H, d); 10.0 (1H, peak exchangeable with CF$_3$COOD).

Example 14

2-[(2,2,2-Trifluoroethoxy)methyl]-4(3H)-pteridinone a) (2,2,2-Trifluoroethoxy)acetonitrile

At about 50° C., 26.4 g (0.40 mole) of 85% potassium hydroxide are solubilized in 100 g (1.0 mole) of 2,2,2-trifluoroethanol. After cooling at 25° C., 37.8 g (0.50 mole) of chloroacetonitrile are added dropwise to this solution. The temperature rises slowly to 40° C. and a precipitate appears. The reaction mixture is then brought gradually to 60° C.; after the addition of 300 ml of heptane, it is then brought to reflux. The whole of the vapour is condensed by means of a Dean and Stark apparatus. The lower phase of the condensate is separated after settling has taken place and distilled at atmospheric pressure. Yld: 19.6 g (28%), b.p. 125°-140° C.
NMR (CDCl$_3$): δ=3.9 (2H, q); 4.4 (2H, s).

b) Methyl 2-(2,2,2-trifluoroethoxy)acetimidate

Obtained using the procedure described in section a of Example 2, starting with 19.6 g (0.141 mole) of (2,2,2-trifluoroethoxy)acetonitrile and 0.3 g (0.013 gram-atom) of sodium in 95 ml of methanol. Reaction time: 24 hours. Yld: 15.6 g (65%), b.p.$_{15}$44°-47° C.

NMR (CDCl$_3$): δ=3.8 (3H, s); 3.9 (2H, q); 4.0 (2H, s); 7.7 (1H, peak exchangeable with D$_2$O)

c) 2-(2,2,2-Trifluoroethoxy)acetamidine

Obtained using the procedure described in section b of Example 2, starting with 15.6 g (0.091 mole) of methyl 2-(2,2,2-trifluoroethoxy)acetimidate and 7.7 g (0.455 mole) of ammonia in 225 ml of absolute ethanol. Reaction time: 24 hours. Yld: 14.2 g (quantitative).

d) 4-Amino-2-[(2,2,2-trifluoroethoxy)methyl]pteridine

Obtained using the procedure described in section c of Example 2, starting with 7.2 g (0.060 mole) of 3-amino-2-pyrazinecarbonitrile and 14.2 g (0.091 mole) of 2-(2,2,2-trifluoroethoxy)acetamidine in 230 ml of absolute ethanol. Refluxing time: 7 hours. Yld: 6.5 g (42%), m p. 145°-147° C. (ethyl acetate).

| Percentage analysis: C$_9$H$_8$F$_3$N$_5$O (FW = 259.19) | | | | |
|---|---|---|---|---|
| | C % | H % | F % | N % |
| calculated | 41.71 | 3.11 | 21.99 | 27.02 |
| found | 41.92 | 2.96 | 21.78 | 26.93 |

NMR (DMSO-d$_6$): δ=4.2 (2H, q); 4.6 (2H, s); 8.3 (2H, peak exchangeable with CF$_3$COOD); 8.7 (1H, m); 9.0 (1H, m).

e) 2-[(2,2,2-Trifluoroethoxy)methyl]-4(3H)-pteridinone

Obtained using the procedure described in section d of Example 2, starting with 5.0 g (0.0193 mole) of 4-amino-2-[(2,2,2-trifluoroethoxy)methyl]pteridine in 105 ml of 5% aqueous sodium hydroxide. Heating time: 1 hour 30 minutes at 80° C. Yld: 2.5 g (50%), m.p. 165°-167° C. (ethyl acetate).

| Percentage analysis: C$_9$H$_7$F$_3$N$_4$O$_2$ (FW = 260.18) | | | | |
|---|---|---|---|---|
| | C % | H % | F % | N % |
| calculated | 41.55 | 2.71 | 21.91 | 21.53 |
| found | 41.53 | 2.68 | 21.78 | 21.32 |

IR: $\bar{\nu}$(C=O)=1690 cm$^{-1}$
NMR (DMSO-d$_6$+CF$_3$COOD); δ=4.2 (2H, q); 4.6 (2H, s); 8.7 (1H, d); 8.9 (1H, d).

Example 15

2-[(4-Chlorophenoxy)methyl]-4(3H)-pteridinone a) 4-Amino-2-[(4-chlorophenoxy)methyl]pteridine

Obtained using the procedure described in section c of Example 2, starting with 10.7 g (0.089 mole) of 3-amino-2-pyrazinecarbonitrile and 24.5 g (0.133 mole) of 2-(4-chlorophenoxy)acetamidine [prepared according to C. Djerassi and C. R. Scholz, U.S. Pat. No. 2,517,468; C.A. 1951, 45, 661f] in 320 ml of absolute ethanol. Refluxing time: 7 hours. Yld: 21.5 g (84%), m.p. 246°-248° C. (N,N-dimethylformamide).

| Percentage analysis: C$_{13}$H$_{10}$ClN$_5$O (FW = 287.71) | | | | |
|---|---|---|---|---|
| | C % | H % | Cl % | N % |
| calculated | 54.27 | 3.50 | 12.32 | 24.34 |
| found | 54.25 | 3.50 | 12.37 | 24.33 |

NMR (DMSO-d$_6$): δ=5.1 (2H, s); 6.9 (2H, d); 7.3 (2H, d); 8.3 (2H, peak exchangeable with CF$_3$COOD); 8.7 (1H, d); 9.0 (1H, d).

b) 2-[(4-chlorophenoxy)methyl]-4(3H)-pteridinone

Obtained using the procedure described in section b of Example 9, starting with 17.5 g (0.0608 mole) of crude 4-amino-2-[(4-chlorophenoxy)methyl]pteridine in 1750 ml of 5% aqueous sodium hydroxide. Heating time: 1 hours 30 minutes under reflux. Yld: 8.7 g (50%), m.p. 267°-269° C. (ethanol/N,N-dimethylformamide).

| Percentage analysis: C$_{13}$H$_9$ClN$_4$O$_2$ (FW = 288.69) | | | | |
|---|---|---|---|---|
| | C % | H % | Cl % | N % |
| calculated | 54.09 | 3.14 | 12.28 | 19.41 |
| found | 54.04 | 2.94 | 12.42 | 19.20 |

IR: $\bar{\nu}$(C=O)=1675 cm$^{-1}$
NMR (CF$_3$COOD): δ=5.5 (2H, s); 7.1 (2H, d); 7.4 (2H, d); 9.2 (1H, d); 9.3 (1H, d).

Example 16

2-[(3,4-Dichlorophenoxy)methyl]-4(3H)-pteridinone a) Methyl 2-(3,4-dichlorophenoxy)acetimidate 30.3 g (0.150 mole) of (3,4-dichlorophenoxy)-acetonitrile [prepared according to R. W. Fuller et al., J. Med. Chem. 1973, 16, 101] are added to a solution of sodium methoxide in methanol, obtained by reaction of 0.34 g (0.015 gram-atom) of sodium in 300 ml of methanol. The reaction mixture is stirred for 36 hours at room temperature. The sodium methoxide is then neutralized with a stream of carbon dioxide, and the reaction mixture is thereafter concentrated to dryness under reduced pressure. The residue obtained is taken up with methylene chloride. The inorganic products are removed by filtration; the organic filtrate is concentrated to dryness under reduced pressure and the residue is recrystallized from isopropyl ether. Yld: 28.2 g (80%), m.p. 55°–56° C.

b) 2-(3,4-Dichlorophenoxy)acetamidine

Obtained using the procedure described in section b of Example 2, starting with 28.2 g (0.12 mole) of methyl 2-(3,4-dichlorophenoxy)acetimidate and 10.2 g (0.60 mole) of ammonia in 480 ml of absolute ethanol. Reaction time: 3 hours. Yld: 26.3 g (quantitative).

c) 4-Amino-2-[(3,4-dichlorophenoxy)methyl]pteridine

Obtained using the procedure described in section c of Example 2, starting with 9.6 g (0.080 mole) of 3-amino-2-pyrazinecarbonitrile and 26.3 g (0.12 mole) of 2-(3,4-dichlorophenoxy)acetamidine in 520 ml of absolute ethanol. Refluxing time: 3 hours. Yld: 18.0 g (70%), m.p. 261°–263° C. (ethanol/N,N-dimethylformamide).

| Percentage analysis: $C_{13}H_9Cl_2N_5O$ (F = 322.15) | | | | |
|---|---|---|---|---|
| | C % | H % | Cl % | N % |
| calculated | 48.47 | 2.82 | 22.01 | 21.74 |
| found | 48.50 | 2.85 | 22.31 | 21.65 |

NMR ($CF_3COOD$): δ=5.4 (2H, s); 6.9–7.6 (3H, m); 9.2 (2H, s).

d) 2-[(3,4-Dichlorophenoxy)methyl]-4(3H)-pteridinone

Obtained using the procedure described in section b of Example 9, starting with 15.0 g (0.0466 mole) of 4-amino-2-[(3,4-dichlorophenoxy)methyl]pteridine in 1500 ml of 5% aqueous sodium hydroxide. Heating time: 6 hours under reflux. Yld: 10.0 g (66%), m.p. 285°–287° C. (ethanol/N,N-dimethylformamide).

| Percentage analysis: $C_{13}H_8Cl_2N_4O_2$ (FW = 323.14) | | | | |
|---|---|---|---|---|
| | C % | H % | Cl % | N % |
| calculated | 48.32 | 2.50 | 21.94 | 17.34 |
| found | 48.55 | 2.51 | 21.91 | 16.89 |

IR: $\bar{\nu}$(C=O)=1690 $cm^{-1}$

NMR ($CF_3COOD$): δ=5.6 (2H, s); 7.0–7.7 (3H, m); 9.3 (1H, d); 9.4 (1H, d).

Example 17

2-[(4-Methoxyphenoxy)methyl]-4(3H)-pteridinone a) Methyl 2-(4-methoxyphenoxy)acetimidate Obtained using the procedure described in section a of Example 16, starting with 27.3 g (0.167 mole) of (4-methoxyphenoxy)acetonitrile [prepared according to K. J. S. Arora et al., J. Chem. Soc. C 1971, 2865] and 0.38 g (0.0167 gram-atom) of sodium in 275 ml of methanol. Reaction time: 24 hours. Yld: 23.9 g (73%), m.p. 95°–96° C. (isopropyl ether).

b) 2-(4-Methoxyphenoxy)acetamidine 23.9 g (0.122 mole) of methyl 2-(4-methoxyphenoxy)acetimidate are added to a solution, maintained at 10° C., of 10.4 g (0.61 mole) of ammonia in 480 ml of absolute ethanol. The reaction mixture is left for 2 days at room temperature and the excess ammonia is then driven off with a stream of nitrogen. The solution obtained is used in the next step without further purification.

c) 4-Amino-2-[(4-methoxyphenoxy)methyl]pteridine

Obtained using the procedure described in section c of Example 2, starting with 9.8 g (0.082 mole) of 3-amino-2-pyrazinecarbonitrile and the above solution of 2-(4-methoxyphenoxy)acetamidine in absolute ethanol. Refluxing time: 2 hours. Yld: 5.5 g (24%), m.p. 238°–240° C. (ethanol/N,N-dimethylformamide).

| Percentage analysis: $C_{14}H_{13}N_5O_2$ (FW = 283.29) | | | |
|---|---|---|---|
| | C % | H % | N % |
| calculated | 59.36 | 4.63 | 24.72 |
| found | 59.21 | 4.62 | 24.71 |

NMR (DMSO-$d_6$): δ=3.7 (3H, s); 5.0 (2H, s); 6.9 (4H, s); 8.3 (2H, peak exchangeable with $CF_3COOD$); 8.8 (1H, d); 9.0 (1H, d).

d) 2-[(4-Methoxyphenoxy)methyl]-4(3H)-pteridinone

Obtained using the procedure described in section b of Example 9, starting with 5.5 g (0.0194 mole) of 4-amino-2-[(4-methoxyphenoxy)methyl]pteridine in 150 ml of 5% aqueous sodium hydroxide. The solid obtained is taken up in dilute sodium hydroxide for purification. The insoluble portion is removed by filtration. The filtrate is acidified with acetic acid to pH 5.5. The precipitate formed is isolated by filtration; it is finally recrystallized from a mixture of ethanol and N,N-dimethylformamide. Yld: 1.7 g (31%), m.p. 233°–234° C.

| Percentage analysis: $C_{14}H_{12}N_4O_3$ (FW = 284.27) | | | |
|---|---|---|---|
| | C % | H % | N % |
| calculated | 59.15 | 4.26 | 19.71 |
| found | 59.21 | 4.34 | 19.39 |

IR: $\bar{\nu}$(C=O)=1690 $cm^{-1}$

NMR (DMSO-$d_6$): δ=3.7 (3H, s); 5.0 (2H, s); 6.8 (2H, d); 7.0 (2H, d); 8.8 (1H, d); 9.0 (1H, d); 13.0 (1H, peak exchangeable with $CF_3COOD$).

Example 18

2-[(4-Methoxyphenoxy)methyl]-4(3H)-pteridinone a) 4-Amino-2-[(4-methylphenoxy)methyl]pteridine Obtained using the procedure described in section c of Example 2, starting with 6.9 g (0.057 mole) of 3-amino-2-pyrazinecarbonitrile and 14.1 g (0.086 mole) of 2-(4-methylphenoxy)acetamidine [prepared according to C. Djerassi and C. R. Scholz, U.S. Pat. No. 2,517,468; C.A. 1951, 45, 661f] in 350 ml of absolute ethanol. Refluxing time: 2 hours. Yld: 2.6 g (17%), m.p. 225°–227° C. (acetone/ethanol).

| Percentage analysis: $C_{14}H_{13}N_5O$ (FW = 267.29) | | | |
|---|---|---|---|
| | C % | H % | N % |
| calculated | 62.91 | 4.90 | 26.20 |
| found | 63.22 | 4.93 | 26.23 |

NMR (DMSO-$d_6$): δ=2.2 (3H, s); 5.0 (2H, s); 6.8 (2H, d); 7.0 (2H, d); 8.3 (2H, peak exchangeable with $CF_3COOD$); 8.8 (1H, d); 9.0 (1H, d).

b) 2-[(4-Methylphenoxy)methyl]-4(3H)-pteridinone

Obtained using the procedure described in section b of Example 9, starting with 2.5 g (0.0094 mole) of 4- amino-2-[(4-methylphenoxy)methyl]pteridine in 68.1 ml of 5% aqueous sodium hydroxide. Heating time: 3 hours 15 minutes at 85° C. Yld: 1.3 g (52%), m.p. 232°–233° C. (ethanol/N,N-dimethylformamide).

| Percentage analysis: $C_{14}H_{12}N_4O_2$ (FW = 268.28) | | | |
|---|---|---|---|
| | C % | H % | N % |
| calculated | 62.68 | 4.51 | 20.88 |
| found | 62.89 | 4.54 | 21.29 |

IR: $\bar{\nu}(C=O) = 1690$ cm$^{-1}$
NMR (DMSO-d$_6$): $\delta = 2.2$ (3H, s); 5.0 (2H, s); 6.9 (2H, d); 7.1 (2H, d); 8.8 (1H, d); 9.0 (1H, d); 12.9 (1H, peak exchangeable with CF$_3$COOD).

Example 19

2-Benzylthiomethyl-4(3H)-pteridinone a) 4-Amino-2-(benzylthiomethyl)pteridine

A suspension of 2.3 g (0.019 mole) of 3-amino-2-pyrazinecarbonitrile and 5.2 g (0.029 mole) of 2-(benzylthio)acetamidine [prepared according to J. M. McManus, J. Heterocycl. Chem. 1968, 5, 137] in 150 ml of absolute ethanol is refluxed for 2 hours. After cooling, the solution obtained is concentrated to dryness under reduced pressure. The residue is washed with isopropyl ether and dried under reduced pressure. An amorphous solid is obtained, and is used in the next step without further purification. Yld: 5.4 g (quantitative).

b) 2-Benzylthiomethyl-4(3H)-pteridinone

Obtained using the procedure described in section b of Example 9, starting with 5.4 g (0.019 mole) of 4-amino-2-(benzylthiomethyl)pteridine in 400 ml of 5% aqueous sodium hydroxide. Reaction time: 7 hours at 85° C. Yld: 1.7 g (31%), m.p. 224°–226° C. (ethanol/N,N-dimethylformamide).

| Percentage analysis: $C_{14}H_{12}N_4OS$ (FW = 284.34) | | | | |
|---|---|---|---|---|
| | C % | H % | N % | S % |
| calculated | 59.14 | 4.25 | 19.70 | 11.28 |
| found | 58.92 | 4.35 | 20.02 | 11.10 |

IR: $\bar{\nu}(C=O) = 1690$ cm$^{-1}$
NMR (DMSO-d$_6$): $\delta = 3.6$ (2H, s exchangeable with CF$_3$COOD); 3.9 (2H, s); 7.0–7.5 (5H, m); 8.8 (1H, d); 9.0 (1H, d); 12.8 (1H, peak exchangeable with CF$_3$COOD).

Example 20

2-Ethoxymethyl-6-methyl-4(3H)-pteridinone a) Ethyl 2-ethoxyacetimidate

A solution of 604 g (8.0 moles) of chloroacetonitrile in 1200 ml of absolute ethanol is added dropwise to a solution, maintained at 80° C., of sodium ethoxide in ethanol, obtained from 193.2 g (8.4 gram-atoms) of sodium and 4 l of absolute ethanol. The reaction mixture is allowed to return to room temperature; stirring is continued for 2 days. The excess sodium ethoxide is then neutralized with a stream of carbon dioxide. The precipitate formed is removed by filtration and washed with ether. The filtrate and the ethereal wash solution are combined and concentrated under reduced pressure. A new precipitate is formed and is removed by filtration. The filtrate is distilled under reduced pressure Yld: 597.6 g (57%), b.p.$_{15-24}$47°–52° C.

NMR (CDCl$_3$ + CF$_3$COOD): $\delta = 1.1$ (3H, t); 1.2 (3H, t); 3.4 (2H, q); 3.7 (2H, s); 4.1 (2H, q).

b) 2-Ethoxyacetamidine

Obtained using the procedure described in section b of Example 17, starting with 29.4 g (0.224 mole) of ethyl 2-ethoxyacetimidate and 21.2 g (1.24 moles) of ammonia in 590 ml of absolute ethanol.

c) 4-Amino-2-ethoxymethyl-6-methylpteridine

A suspension of 15.1 g (0.113 mole) of 3-amino-6-methyl-2-pyrazinecarbonitrile [prepared according to E. C. Taylor et al., J. Am. Chem. Soc. 1973, 95, 6413] in the above ethanolic solution of 2-ethoxyacetamidine is refluxed for 2 hours. After cooling, the solution obtained is concentrated to dryness under reduced pressure. The residue is purified by washing with acetone and recrystallization from a mixture of acetone and isopropyl ether Yld: 8.4 g (34%), m.p. 166°–168° C.

| Percentage analysis: $C_{10}H_{13}N_5O$ (FW = 219.25) | | | |
|---|---|---|---|
| | C % | H % | N % |
| calculated | 54.78 | 5.98 | 31.94 |
| found | 54.63 | 6.02 | 32.10 |

NMR (DMSO-d$_6$): $\delta = 1.1$ (3H, t); 2.6 (3H, s); 3.6 (2H, q); 4.4 (2H, s); 8.0 (2H, peak exchangeable with CF$_3$COOD); 8,9 (1H, s).

d) 2-Ethoxymethyl-6-methyl-4(3H)-pteridinone

A suspension of 7.4 g (0.0338 mole) of 4-amino-2-ethoxymethyl-6-methylpteridine in 148 ml of 5% aqueous sodium hydroxide is brought slowly to 85° C. and maintained at this temperature for 2 hours. A further 592 ml of 5% aqueous sodium hydroxide are then added and heating is continued at 85° C for 1 hour. After cooling, the solution obtained is acidified with acetic acid to pH 5.5, and is then extracted with dichloromethane. The organic extracts are dried over sodium sulphate and concentrated to dryness under reduced pressure. The solid residue is recrystallized from acetone in the presence of Norit. Yld: 4.9 g (66%), m.p. 181°–183° C.

| Percentage analysis: $C_{10}H_{12}N_4O_2$ (FW = 220.23) | | | |
|---|---|---|---|
| | C % | H % | N % |
| calculated | 54.54 | 5.49 | 25.44 |
| found | 54.39 | 5.49 | 25.22 |

IR: $\bar{\nu}(C=O) = 1670$ cm$^{-1}$
NMR (DMSO-d$_6$): $\delta = 1.2$ (3H, t); 2.6 (3H, s); 3.6 (2H, q); 4.4 (2H, s); 8.8 (1H, s); 13.8 (1H, peak exchangeable with CF$_3$COOD).

Example 21

2-[(2-Acetoxyethoxy)methyl]-4(3H)-pteridinone a) Ethyl 2-(2-hydroxyethoxy)acetimidate 55.7 g (0.389 mole) of (2-acetoxyethoxy)acetonitrile [prepared according to S. W. Schneller et al., Croat. Chem. Acta 1986, 59, 307] are added to a solution, maintained at 10° C, of sodium ethoxide in ethanol, obtained from 0.89 g (0.0389 gram-atom) of sodium and 560 ml of absolute ethanol. The reaction mixture is allowed to return to room temperature; stirring is continued for 3 days. The excess sodium ethoxide is then neutralized with a stream of carbon dioxide. The precipitate formed is removed by filtration and washed with ether. The filtrate and the ethereal wash solution are combined and concentrated under reduced pressure at 30° C. The residue obtained is taken up with 800 ml of ether. On cooling, a new precipitate is formed and removed by filtration. The filtrate is concentrated under reduced pressure at a temperature below 30° C. The liquid obtained is used in the next step without further purification. Yld: 39.2 g (68%).

NMR (CDCl$_3$+D$_2$O): δ=1.3 (3H, t); 3.3–3.9 (4H, m); 3.9 (2H, s); 4.2 (2H, q).

b) 2-(2-Hydroxyethoxy)acetamidine

Obtained using the procedure described in section b of Example 17, starting with 39.2 g (0.266 mole) of ethyl 2-(2-hydroxyethoxy)acetimidate and 22.6 g (1.33 moles) of ammonia in 1080 ml of absolute ethanol.

c) 4-Amino-2-[(2-hydroxyethoxy)methyl]pteridine

Obtained using the procedure described in section c of Example 2, starting with 16.0 g (0.133 mole) of 3-amino-2-pyrazinecarbonitrile and the above solution of 2-(2-hydroxyethoxy)acetamidine in absolute ethanol. Refluxing time: 2 hours 30 minutes. Yld: 20.5 g (70%), m.p. 149°–151° C. (ethanol). An analytical sample was obtained by recrystallization from a mixture of acetone and ethanol. M.p. 159°–161° C.

| Percentage analysis: C$_9$H$_{11}$N$_5$O$_2$ (FW = 221.22) | | | |
|---|---|---|---|
| | C % | H % | N % |
| calculated | 48.86 | 5.01 | 31.66 |
| found | 48.83 | 5.02 | 31.32 |

NMR (DMSO-d$_6$): δ=3.6 (4H, s); 4.5 (2H, s); 4.9 (1H, peak exchangeable with CF$_3$COOD); 8.3 (2H, peak exchangeable with CF$_3$COOD); 8.8 (1H, d); 9.0 (1H, d).

d) 2-[(2-Acetoxyethoxy)methyl]-4(3H)-pteridinone

A solution of 10.0 g (0.0452 mole) of 4-amino-2-[(2-hydroxyethoxy)methyl]pteridine in 350 ml of 5% aqueous sodium hydroxide is brought gradually to 85° C and maintained at this temperature for 1 hour 30 minutes. After cooling, the solution obtained is acidified with acetic acid to pH 5.5, and is then concentrated to dryness under reduced pressure. The residue is taken up in 500 ml of isopropanol. The insoluble inorganic portion is removed by filtration. The isopropanolic solution is concentrated to dryness under reduced pressure. The solid residue is treated with 250 ml of acetic anhydride and this mixture is refluxed for 1 hour. After cooling, inorganic salts are removed by filtration; the filtrate is concentrated to dryness under reduced pressure. The residue is purified by 4 successive recrystallizations from ethanol in the presence of Norit. Yld: 1.2 g (10%), m.p. 157°–159° C.

| Percentage analysis: C$_{11}$H$_{12}$N$_4$O$_4$ (FW = 264.24) | | | |
|---|---|---|---|
| | C % | H % | N % |
| calculated | 50.00 | 4.58 | 21.20 |
| found | 50.05 | 4.75 | 21.08 |

IR: $\bar{v}$(C=O)=1690 and 1720 cm$^{-1}$
NMR (DMSO-d$_6$): δ=2.0 (3H, s); 3.7–4.0 (2H, m); 4.1–4.4 (2H, m); 4.5 (2H, s); 8.8 (1H, d); 9.0 (1H, d); 12.6 (1H, peak exchangeable with CF$_3$COOD).

Example 22

2-[(4-Acetyl-3-hydroxy-2-propylphenoxy)methyl]-4(3H)-pteridinone a) Ethyl 2-(4-acetyl-3-hydroxy-2-propylphenoxy)acetimidate hydrochloride

Obtained using the procedure described in section a of Example 6, starting with 30.4 g (0.130 mole) of (4-acetyl-3-hydroxy-2-propylphenoxy)acetonitrile [prepared according to W. S. Marshall et al., J. Med. Chem. 1987, 30, 682] and 6.6 g (0.143 mole) of absolute ethanol in 500 ml of ether. Reaction time: 16 hours. After the reaction mixture has been poured into 1 l of ether, the reaction product is isolated by filtration. Yld: 40.0 g (97%), m.p. 157°–159° C.

NMR (DMSO-d$_6$): δ=0.9 (3H, t); 1.1–1.9 (2H, m); 1.4 (3H, t); 2.4–2.9 (2H, m); 2.6 (3H, s); 4.6 (2H, q); 5.3 (2H, s); 6.7 (1H, d); 7.8 (1H, d); 10.8 (2H, peak exchangeable with CF$_3$COOD); 12.8 (1H, s exchangeable with CF$_3$COOD).

b) Ethyl 2-(4-acetyl-3-hydroxy-2-propylphenoxy)acetimidate 10.2 g (0.121 mole) of sodium hydrogen carbonate are added to a suspension of 40.0 g (0.127 mole) of ethyl 2-(4-acetyl-3-hydroxy-2-propylphenoxy)acetimidate hydrochloride in 1 l of chloroform, and this mixture is stirred for 1 hour. The solid is removed by filtration and the filtrate is concentrated to dryness under reduced pressure. The residue obtained is extracted with a mixture of 100 ml of hexane and 100 ml of isopropyl ether under reflux. This extract, concentrated under reduced pressure, is recrystallized from hexane. Yld: 25.0 g (70%), m.p. 50°–52° C.

NMR (CDCl$_3$+D$_2$O): δ=1.0 (3H, t); 1.1–1.9 (2H, m); 1.4 (3H, t); 2.6 (3H, s); 2.7 (2H, t); 4.3 (2H, q); 4.7 (2H, s); 6.3 (1H, d); 7.6 (1H, d); 12.7 (1H, s partially exchanged).

c) 2-(4-Acetyl-3-hydroxy-2-propylphenoxy)acetamidine

Obtained using the procedure described in section b of Example 17, starting with 25.0 g (0.0895 mole) of ethyl 2-(4-acetyl-3-hydroxy-2-propylphenoxy)acetimidate and 7.6 g (0.45 mole) of ammonia in 300 ml of absolute ethanol.

d) 2-[(4-Acetyl-3-hydroxy-2-propylphenoxy)methyl]-4-aminopteridine

Obtained using the procedure described in section c of Example 2, starting with 3.6 g (0.030 mole) of 3-amino-2-pyrazinecarbonitrile and the above solution of 2-(4-acetyl-3-hydroxy-2-propylphenoxy)acetamidine in absolute ethanol. Refluxing time: 6 hours. Yld: 3.2 g (30%), m.p. 178°–180° C. (ethanol/N,N-dimethylformamide).

An analytical sample was obtained by a further recrystallization from a mixture of ethanol and N,N-dimethylformamide. M.p. 179°–181° C.

| Percentage analysis: C$_{18}$H$_{19}$N$_5$O$_3$ (FW = 353.38) | | | |
|---|---|---|---|
| | C % | H % | N % |
| calculated | 61.18 | 5.42 | 19.82 |

| Percentage analysis: C₁₈H₁₉N₅O₃ (FW = 353.38) | | | |
|---|---|---|---|
| | C % | H % | N % |
| found | 60.96 | 5.59 | 19.99 |

IR: $\bar{v}$(C=O) = 1640 cm⁻¹

NMR (DMSO-d₆): δ = 0.9 (3H, t); 1.1–1.9 (2H, m); 2.5 (3H, s); 2.5–2.9 (2H, m); 5.2 (2H, s); 6.6 (1H, d); 7.7 (1H, d); 8.3 (2H, peak exchangeable with CF₃COOD); 8.8 (1H, d); 9.0 (1H, d); 13.9 (1H, peak exchangeable with CF₃COOD).

e)
2-[(4-Acetyl-2-hydroxy-3-propylphenoxy)methyl]-4(3H)-pteridinone

Obtained using the procedure described in section d of Example 2, starting with 1.6 g (0.0045 mole) of 2-[(4-acetyl-3-hydroxy-2-propylphenoxy)methyl]-4-aminopteridine in 32 ml of 5% aqueous sodium hydroxide. Heating time: 1 hour at 90° C. Yld: 1.0 g (63%), m.p. 224°–226° C. (ethanol/N,N-dimethylformamide).

| Percentage analysis: C₁₈H₁₈N₄O₄ (FW = 354.37) | | | |
|---|---|---|---|
| | C % | H % | N % |
| calculated | 61.01 | 5.12 | 15.81 |
| found | 61.12 | 5.23 | 15.89 |

IR: $\bar{v}$(C=O) = 1670 and 1690 cm⁻¹

NMR (DMSO-d₆): δ = 0.9 (3H, t); 1.0–2.0 (2H, m); 2.4–2.9 (2H, m); 2.5 (3H, s); 5.2 (2H, s); 6.7 (1H, d); 7.7 (1H, d); 8.8 (1H, d); 8.9 (1H, d), 12.8 (1H, s exchangeable with CF₃COOD); 13.0 (1H, peak exchangeable with CF₃COOD).

Example 23
7-Hydroxy-2-hydroxymethyl-4(3H)-pteridinone

A mixture of 4.0 g (0.0169 mole) of 2-acetoxymethyl-7-hydroxy-4(3H)-pteridinone, 1.2 g (0.0214 mole) of potassium hydroxide and 5 ml of water in 80 ml of ethanol is refluxed for 4 hours. After cooling, the reaction mixture is filtered. The solid thereby isolated is washed with 30 ml of ethanol and taken up in 160 ml of water. The cloudy solution obtained is clarified by filtration and acidified with acetic acid to pH 3.6. The precipitate formed is isolated by filtration. It is purified by washing with ether and recrystallization from a mixture of ethanol and N,N-dimethylformamide. Yld: 2.0 g (61%), m.p. >300° C.

| Percentage analysis: C₇H₆N₄O₃ (FW = 194.15) | | | |
|---|---|---|---|
| | C % | H % | N % |
| calculated | 43.31 | 3.12 | 28.86 |
| found | 43.27 | 3.37 | 28.92 |

IR: $\bar{v}$(C=O) = 1640 and 1675 cm⁻¹

NMR (DMSO-d₆ + CF₃COOD): δ = 4.4 (2H, s); 7.9 (1H, s).

Example 24
7-Hydroxy-2-methoxymethoxymethyl-4(3H)-pteridinone a) 2-(Methoxymethoxy)acetamidine Obtained using the procedure described in section b of Example 17, starting with 14.4 g (0.108 mole) of methyl 2-(methoxymethoxy)acetimidate and 7.6 g (0.446 mole) of ammonia in 146 ml of anhydrous methanol. Reaction time: 3 days.

b)
4-Amino-7-methoxy-2-(methoxymethoxymethyl)pteridine

Obtained using the procedure described in section c of Example 2, starting with 11.2 g (0.0725 mole) of 3-amino-5-chloro-2-pyrazinecarbonitrile[prepared according to E. C. Taylor et al. 1975, 40, 2341] and the above solution of 2-(methoxymethoxy)acetamidine in methanol. Refluxing time: 5 hours. Yld: 13.2 g (72%), m.p. 193°–195° C.

NMR: (DMSO-d₆): δ = 3.3 (3H, s); 4.0 (3H, s); 4.5 (2H, s); 4.7 (2H, s), 7.9 (2H, peak exchangeable with CF₃COOD); 8.4 (1H, s).

c)
4-Amino-7-hydroxy-2-(methoxymethoxymethyl)pteridine 8.1 g (0.0322 mole) of 4-amino-7-methoxy-2-(methoxymethoxymethyl)pteridine are added to a solution of 3.2 g (0.080 mole) of sodium hydroxide in 130 ml of water. The suspension obtained is heated at 80° C. for 2 hours. After filtration while hot, the solution is allowed to return to room temperature and is then acidified with acetic acid. The precipitate formed is isolated by filtration. It is purified by washing with water and then with acetone and is recrystallized from a mixture of methanol and N,N-dimethylformamide. Yld: 4.4 g (58%), m.p. 210°–212° C.

| Percentage analysis: C₉H₁₁N₅O₃ (FW = 237.22) | | | |
|---|---|---|---|
| | C % | H % | N % |
| calculated | 45.57 | 4.67 | 29.52 |
| found | 45.30 | 4.53 | 29.56 |

NMR (DMSO-d₆): δ = 3.3 (3 H, s); 4.4 (2H, s); 4.7 (2H, s); 7.7 (2H, peak exchangeable with CF₃COOD); 7.9 (1H, s); 12.7 (1H, peak exchangeable with CF₃COOD).

d)
7-Hydroxy-2-methoxymethoxymethyl-4(3H)-pteridinone 1.1 g (0.00464 mole) of 4-amino-7-hydroxy-2-(methoxymethoxymethyl)pteridine is added to a solution of 1.5 g (0.0267 mole) of potassium hydroxide in 20 ml of water. The mixture is refluxed for 8 hours. After cooling, the reaction mixture is acidified with 10% hydrochloric acid to pH 5.5. The precipitate formed is isolated by filtration and washed with water. It is extracted with a mixture of 50 ml of ethanol and 60 ml of N,N-dimethylformamide under reflux. This extract, concentrated under reduced pressure, is recrystallized from a mixture of ethanol and N,N-dimethylformamide. Yld: 0.2 g (18%), m.p. 224°–226° C. (ethanol).

| Percentage analysis: C₉H₁₀N₄O₄ (FW = 238.20) | | | |
|---|---|---|---|
| | C % | H % | N % |
| calculated | 45.38 | 4.23 | 23.52 |
| found | 45.15 | 4.11 | 23.59 |

IR: $\bar{v}$(C=O) = 1625 cm⁻¹

NMR: (DMSO-d$_6$): δ=3.3 (3H, s); 4.4 (2H, s); 4.7 (2H, s); 7.9 (1H, s); 12.8 (2H, peak exchangeable with CF$_3$COOD).

Example 25

2-(Ethoxymethyl)-4(3H)-pteridinone a) 6-Amino-2-(ethoxymethyl)-4(3H)-pyrimidinone A stream of ammonia is bubbled into a solution, maintained at 0° C., of 75.7 g (0.577 mole) of ethyl 2-ethoxyacetimidate in 650 ml of absolute ethanol so as to dissolve 39.1 g (2.30 moles) of the gas. The solution obtained is left stirring at room temperature for 2 days. The excess ammonia is then driven off with a stream of nitrogen. The reaction mixture is treated with 75.0 g (0.383 mole) of ethyl (1-ethoxyformimidoyl)acetate hydrochloride (prepared according to J. J. Ursprung, U.S. Pat. No. 3,337,579; C.A. 1968, 68, 68986k), and then, at about 0° C., with 27.3 g (0.401 mole) of sodium ethoxide. After 15 minutes at 0° C., the suspended solid is removed by filtration; the filtrate is stirred for 24 hours at room temperature and is then refluxed for 2 hours. This solution is concentrated by the removal of 425 ml of ethanol by means of a Dean and Stark apparatus; it is then cooled to about −20° C. The precipitate formed is isolated by filtration and washed with ethyl ether. The solid obtained is dried and used in the next step without further purification. Yld: 39.5 g (61%), m.p. 224°-226° C. An analytical sample was obtained by recrystallization from a mixture of isopropanol and isopropyl ether. M.p. 228° C.

| Percentage analysis: C$_7$H$_{11}$N$_3$O$_2$ (FW = 169.18) | | | |
|---|---|---|---|
| | C % | H % | N % |
| calculated | 49.70 | 6.55 | 24.84 |
| found | 49.90 | 6.21 | 24.59 |

IR: $\bar{\nu}$(C=O)=1610 cm$^{-1}$

NMR (DMSO-d$_6$): δ=1.1 (3H, t); 3.5 (2H, q); 4.1 (2H, s); 4.9 (1h,s); 6.4 (2H, s exchangeable with CF$_3$COOD); 11.2 (1H, s exchangeable with CF$_3$COOD).

b) 6-Amino-2-(ethoxymethyl)-5-nitroso-4(3H)-pyrimidinone 17.7 g (0.256 mole) of sodium nitrite are added to a solution of 39.5 g (0.233 mole) of 6-amino-2-(ethoxymethyl)-4(3H)-pyrimidinone in 336 ml (0.336 mole) of 1N sodium hydroxide. A solution of 17.9 ml (0.320 mole) of 96% sulphuric acid diluted in 179 ml of water is then added dropwise at between 0° and 5° C. The precipitate formed is isolated by filtration immediately after completion of the addition. The solid obtained is washed with cold water and then with ethyl ether. After drying, it is used in the next step without further purification. Yld: 46.2 g (quantitative), m.p. 163°-165° C. An analytical sample was obtained by recrystallization from methanol. M.p. 166°-167° C.

| Percentage analysis: C$_7$H$_{10}$N$_4$O$_3$ (FW = 198.18) | | | |
|---|---|---|---|
| | C % | H % | N % |
| Calculated | 42.42 | 5.09 | 28.27 |
| Found | 42.57 | 5.08 | 28.40 |

IR: $\bar{\nu}$(C=O)=1660 cm$^{-1}$

NMR (DMSO-d$_6$): δ=1.15 (3H, t); 3.55 (2H, q); 4.25 (2H, s); 9.15 (1H, peak exchangeable with CF$_3$COOD); 11.15 (1H, peak exchangeable with CF$_3$COOD); 12.15 (1H, peak exchangeable with CF$_3$COOD).

c) 2-(Ethoxymethyl)-4(3H)-pteridinone

A solution of 19.1 g (0.11 mole) of sodium dithionite in 88 ml of water is added dropwise to a suspension, maintained at 20° C., of 10.0 g (0.050 mole) of 6-amino-2-(ethoxymethyl)-5-nitroso-4(3H)-pyrimidinone in 50 ml of water. After being stirred for 30 minutes at room temperature, the reaction mixture, still maintained at 20° C., is treated with 47.9 g (0.33 mole) of a 40% aqueous solution of glyoxal. Stirring is continued for 20 hours at room temperature. The solution obtained is then extracted with dichloromethane. These organic extracts are dried over sodium sulphate and concentrated to dryness under reduced pressure. The solid residue is recrystallized from methanol in the presence of Norit. Yld: 6.5 g (63%), m.p. 168°-169° C. The product is identical to that obtained in Example 1.

Example 26

2-(Ethoxymethyl)-4(3H)-pteridinone a) 5,6-Diamino-2-(ethoxymethyl)-4(3H)-pyrimidinone A mixture of 12.4 g (0.063 mole) of crude 6-amino-2-(ethoxymethyl)-5-nitroso-4(3H)-pyrimidinone, not washed with water, and 1 g of Raney nickel in 430 ml of methanol is introduced into an autoclave. The initial hydrogen pressure is set at 75 bars; the autoclave is stirred for 2 hours at room temperature. After outgassing, the insoluble portion is isolated by filtration and washed with N,N-dimethylformamide. The combined filtrate and washing solution are concentrated to dryness under reduced pressure. The residue is washed with ethyl ether and recrystallized from a mixture of ethanol and water. Yld: 5.0 g (43%), m.p. 173°-175° C.

NMR (DMSO-d$_6$): δ=1.1 (3H, t); 3.5 (2H, q); 4.1 (2H, s); 5.9 (5H, peak exchangeable with CF$_3$COOD).

b) 5,6-Diamino-2-(ethoxymethyl)-4(3H)-pyrimidinone hemimaleate

A mixture of 3.4 g (0.0185 mole) of 5,6-diamino-2-(ethoxymethyl)-4(3H)-pyrimidinone, 4.4 g (0.0379 mole) of maleic acid, 300 ml of absolute ethanol and 100 ml of methanol is brought to reflux. The small insoluble portion is removed by filtration while hot. After cooling, the precipitate formed is isolated by filtration; it is washed with ethyl ether and recrystallized from absolute ethanol. Yld: 2.0 g (45%), m.p. 192°-194° C.

| Percentage analysis: C$_7$H$_{12}$N$_4$O$_2$. ½(C$_4$H$_4$O$_4$) (FW = 242.235) | | | |
|---|---|---|---|
| | C % | H % | N % |
| calculated | 44.63 | 5.83 | 23.13 |
| found | 44.62 | 5.73 | 23.47 |

NMR (DMSO-d$_6$+CF$_3$COOD): δ=1.1 (3H, t); 3.45 (2H, q); 4.15 (2H, s); 6.15 (1H, s).

c) 2-(Ethoxymethyl)-4(3H)-pteridinone 3.5 g (0.024 mole) of a 40% aqueous solution of glyoxal are added to a suspension of 3.7 g (0.020 mole) of 5,6-diamino-2-(ethoxymethyl)-4(3H)-pyrimidinone in 30 ml of water. The mixture is brought gradually to reflux and kept refluxing for 1 hour. After the addition of Norit, refluxing is continued for a further 10 minutes and the reaction mixture is then filtered. The aqueous solution obtained is extracted with dichloromethane. These organic extracts are treated as in section c of Example 25. Yld: 2.5 g (61%), m.p. 168°–169° C. The product is identical to that obtained in Example 1.

We claim:

1. A 4(3H)-pteridinone compound selected from the group consisting of 2-methoxymethyl-4(3H)-pteridinone; 2-ethoxymethyl-4(3)-pteridinone; 2-propoxymethyl-4(3H)-pteridinone; 2-phenoxymethyl-4(3H)-pteridinone; 2-benzyloxymethyl-4(3H)-pteridinone; 2-ethoxymethyl-7-hydroxy-4(3H)-pteridinone; and a pharmaceutically acceptable alkali metal salt thereof.

2. A compound in accordance with claim 1, 2-methoxymethyl-4(3H)-pteridinone, or a pharmaceutically acceptable alkali metal salt thereof.

3. A compound in accordance with claim 1, 2-methoxymethyl-4(3H)-pteridinone, or a pharmaceutically acceptable alkali metal salt thereof.

4. A compound in accordance with claim 1, 2-propoxymethyl-4(3H)-pteridinone, or a pharmaceutically acceptable alkali metal salt thereof.

5. A compound in accordance with claim 1, 2-phenoxymethyl-4(3H)-pteridinone, or a pharmaceutically acceptable alkali metal salt thereof.

6. A compound in accordance with claim 1, 2-benzyloxymethyl-4(3H)-pteridinone, or a pharmaceutically acceptable alkali metal salt thereof.

7. A compound in accordance with claim 1, 2-ethoxymethyl-7-hydroxy-4(3H)-pteridinone, or a pharmaceutically acceptable alkali metal salt thereof.

* * * * *